United States Patent [19]

Hellbach et al.

[11] Patent Number: 4,596,679

[45] Date of Patent: Jun. 24, 1986

[54] MULTIPLE-STEP PROCESS FOR THE PREPARATION OF 3-ISOCYANATOMETHYL-3,5,5-TRIMETHYLCYCLOHEXYLISOCYANATE

[75] Inventors: Hans Hellbach, Lampertheim; Franz Merger, Frankenthal; Friedrich Towae, Ludwigshafen, all of Fed. Rep. of Germany

[73] Assignee: BASF Aktiengesellschaft, Ludwigshafen, Fed. Rep. of Germany

[21] Appl. No.: 599,821

[22] Filed: Apr. 13, 1984

[30] Foreign Application Priority Data

Apr. 23, 1983 [DE] Fed. Rep. of Germany ....... 3314790

[51] Int. Cl.[4] ............................................. C07C 69/00
[52] U.S. Cl. ................................................... 560/344
[58] Field of Search ..................... 260/453 PC, 453 A

[56] References Cited

FOREIGN PATENT DOCUMENTS 0028338 10/1980 European Pat. Off. .

OTHER PUBLICATIONS

Wagner & Zook, Synthetic Org. Chem. (1965) p. 647.
Sandler, Org. Functional Group Prep., vol. 2-II (1971) p. 244.

*Primary Examiner*—Alan Siegel
*Attorney, Agent, or Firm*—William G. Conger; Joseph D. Michaels

[57] ABSTRACT

This invention discloses a non-phosgene process for the preparation of 3-isocyanatomethyl-3,5,5-trimethylcyclohexylisocyanate by the reaction of the precursor diamine with urea and an aliphatic alcohol in the presence of a dialkyl carbonate and an alkyl carbonate. The intermediate diurethane is separated from starting materials and by-products and thermally cleaved to alcohol and diisocyanate which are separated by fractional condensation of the products from the vapor state. This process gives high yields of the desired diisocyanate and lends itself particularly to continuous processing.

11 Claims, No Drawings

MULTIPLE-STEP PROCESS FOR THE PREPARATION OF 3-ISOCYANATOMETHYL-3,5,5-TRIMETHYLCYCLOHEXYLISOCYANATE

BACKGROUND OF THE INVENTION

1. Field of the Invention

This invention pertains to the field of isocyanate synthesis. More specifically, it discloses a non-phosgene process for the preparation of 3-isocyanatomethyl-3,5,5-trimethylcyclohexylisocyanate.

2. Description of the Prior Art 3-isocyanatomethyl-3,5,5-trimethylcyclohexylisocyanate, subsequently referred to also as isophorone diisocyanate or abbreviated as IPDI, is currently prepared solely through the phosgenation of 3-aminomethyl-3,5,5-trimethylcyclohexylamine, subsequently referred to also as isophorone diamine or abbreviated as IPDA, and the subsequent thermal cleavage of the intermediately formed isophorone dicarbamyl chloride into IPDI and hydrogen chloride.

The problems with this process are the high conversion of chlorine via phosgene and carbamyl chloride into hydrogen chloride, the toxicity of the phosgene and the expensive safety problems associated therewith, the corrosiveness of the reaction mixture, and the instability of the solvents that are generally used.

Thus, there have been numerous attempts to prepare isocyanates, primarily aromatic di- and/or polyisocyanates without use of phosgene.

In EP-A No. 28 338 aromatic di- and/or polyisocyanates are prepared in a two-step process, whereby primary aromatic di- and/or polyamines are reacted in the first step with O-alkylcarbamide acid esters in the presence or absence of catalysts and, in some cases, urea and alcohol to form aryldi- and/or polyurethanes, and the ammonia formed in this process may, in some cases, be separated off, and the aryldi- and/or polyurethanes that were obtained can be converted into aromatic di- and/or polyisocyanates in the second reaction step by means of thermal cleavage. In this way, aromatic di- and/or polyisocyanates can be prepared with high yields and without using phosgene.

DE OS No. 31 08 990 describes the preparation of IPDI through the thermal cleavage under pressure of 3-ethoxycarbonylaminomethyl-3,5,5-trimethyl-1-ethoxycarbonylaminocyclohexane in the presence of dibenzyltoluene as a solvent and a catalyst mixture of toluene methylsulfonate and diphenyl tin dichloride. No information is given on obtaining the initial components, isolating and purifying the initial components, possible recovery of the solvent, or on the catalyst mixture. Thus, calculations of the economic feasibility of the process cannot be made.

SUMMARY OF THE INVENTION

The purpose of the invention at hand is to prepare IPDI with a high degree of selectivity at large volume/time yields in an economic and simple manner without utilizing expensive or hazardous initial materials or auxiliaries.

This objective was achieved through a multiple-step process for the preparation of IPDI characterized by (a) reacting IPDA with urea and alcohol in the presence of dialkyl carbonates and/or alkyl esters of carbamic acid and, in some cases, using catalysts to form 3-alkoxycarbonylaminomethyl-3,5,5-trimethyl-1-alkoxycarbonylaminocyclohexane and by simultaneously separating off the resulting ammonia, (b) separating the alcohol, the dialkyl carbonates and/or the alkyl esters of carbamic acid from the resulting reaction mixture and, preferably, recycling same into reaction step (a), (c) evaporating the 3-alkylcarbonyl-aminomethyl-3,5,5-trimethyl-1-alkoxycarbonylaminocyclohexane in an evaporator at temperatures from 200° to 300° C. and a pressure of from 0.1 to 200 mbar, (d) thermally cleaving the vapors at temperatures in excess of 300° C. and at a pressure of from 0.1 to 200 mbar to form IPDI and alcohol in a cleavage reactor, and (e) fractionally condensing the cleavage products.

In a preferred embodiment of the process, the resulting reaction mixture (b) of 3-alkoxycarbonylaminomethyl-3,5,5-trimethyl-1-alkoxycarbonylaminocyclohexane, dialkyl carbonate, and/or alkyl esters of carbamic acid, and alcohol are separated in two steps whereby (i) the alcohol is distilled off in the first step of the reaction until a residual alcohol concentration of from 1 to 30 weight percent based on the total weight of the residual mixture is obtained and said alcohol is returned to reaction step (a), and (ii) in the second step the remaining alcohol, the dialkykl carbonate, and/or the alkyl ester of carbamic acid are separated from the 3-alkoxycarbonylaminomethyl-3,5,5-trimethyl-1-alkoxycarbonylaminocyclohexane by stripping with inert gas, and returned to reaction step (a).

DESCRIPTION OF THE PREFERRED EMBODIMENTS

In the process of the invention, IPDI can be prepared industrially with very good yields and without producing any problems. Particularly advantageous with the multiple-step process is the fact that the initially used and intermediately formed dialkyl carbonates and/or alkyl esters of carbamic acid, and the alcohol can be returned to reaction step (a) and reused without the need for additional expensive purification and recovery processes. Such a process lends itself readily to continuous processing.

In a purely formal sense, the overall balanced equation of the process of the invention can thus be schematically represented by the following:

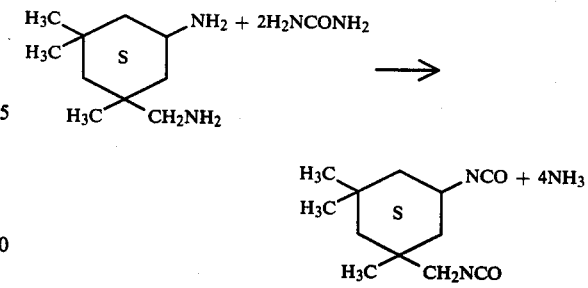

In order to produce the 3-alkoxycarbonylaminomethyl-3,5,5-trimethyl-1-alkoxycarbonylaminocyclohexane in reaction step (a), 1.8 to 2.5, preferably 2.0 to 2.3, moles of urea and 2 to 10, preferably 3 to 6, moles of alcohol are reacted with one mole IPDA in the presence or absence of catalysts at reaction temperatures from 160° to 300° C., preferably from 180° to 250° C., and more preferably from 185° to 240° C., and under a pressure which, depending on the amount of alcohol used, ranges from 0.1 to 60 bar, preferably from 1 to 40 bar. For these reaction conditions, reaction times of from 0.5 to 50, preferably from 3 to 15 hours result.

In principle, all aliphatic alcohols are suitable for use as the alcohols. However, a preferred embodiment is to use those alcohols whose boiling points are sufficiently well removed from the boiling point of the IPDI obtained through thermal cleavage, so that the cleavage products IPDI and alcohol can at least be separated as quantatatively as possible and, on the other hand, so that the resulting 3-alkoxycarbonylaminomethyl-3,5,5-trimethyl-1-alkoxycarbonylaminocyclohexanes, in some cases in addition to isophorone oligourea polyurethanes, can be evaporated with as little decomposition as possible.

For these reasons, alcohols such as methanol, ethanol, n-propanol, n-butanol, iso-butanol, n-pentanol, iso-pentanol, n-hexanol, or mixtures of said alcohols and, in particular, n-propanol, n- and/or iso-butanol are preferably used.

As already discussed, the reaction in reaction step (a) is performed in the presence of dialkylcarbonates in amounts from 1 to 30 mole percent, preferably from 5 to 25 mole percent, or alkyl esters of carbamic acid in amounts from 1 to 20 mole percent, preferably from 5 to 18 mole percent, based on the IPDA. However, it is preferable to use mixtures of dialkyl carbonates and alkyl esters of carbamic acids in the cited quantitative ratios. Preferably, those dialkyl carbonates and/or esters of carbamic acid are used whose alkyl radicals correspond to the alkyl radical of the alcohol being used.

In order to increase the rate of reaction, the 3-alkoxycarbonylaminomethyl-3,5,5-trimethyl-1-alkoxycarbonylaminocyclohexane are prepared in the presence of catalysts. Such catalysts are suitably used in amounts from 0.1 to 20 weight percent, preferably from 0.5 to 10 weight percent, and more preferably from 1 to 5 weight percent, based on the weight of the IPDA. Inorganic or organic compounds are suitable as the catalysts, provided that they contain one or more, preferably one cation, of the metals of groups IA, IB, IIA, IIB, IIIA, IIIB, IVA, IVB, VA, VB, VIB, VIIB and VIIIB of the periodic system defined in accordance with the *Handbook of Chemistry and Physics*, 14th Edition, published by the Chemcial Rubber Publishing Co., 23 Superior Ave. N.E., Cleveland, Ohio, preferably halogenides such as chlorides and bromides, sulfates, phosphates, nitrates, borates, alcoholates, phenylates, sulfonates, oxides, oxide hydrates, hydroxides, carboxylates, chelates, carbonates, and thio- or dithiocarbamates. Typical examples are the cations of the following metals: lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt, and nickel. Preferably, cations of lithium, calcium, aluminum, tin, bismuth, antimony, copper, zinc, titanium, vanadium, chromium, molybdenum, manganese, iron, and cobalt are used. The catalysts can also be used in the form of their hydrates or ammoniates without clearly noticeable disadvantages.

The following compounds are examples of typical catalysts: lithium methanolate, lithium ethanolate, lithium propanolate, lithium butanolate, sodium methanolate, potassium tert-butanolate, magnesium methanolate, calcium methanolate, tin(II)chloride, tin(IV)chloride, lead acetate, lead phosphate, antimony(III)chloride, antimony(V)chloride, aluminum isobutylate, aluminum trichloride, bismuth(III)chloride, copper(II)acetate, copper(II)sulfate, copper(II)nitrate, bis(triphenylphosphinoxide) copper(II)chloride, copper molybdate, silver acetate, gold acetate, zinc oxide, zinc chloride, zinc acetate, zinc acetonyl acetate, zinc octoate, zinc oxalate, zinc hexylate, zinc benzoate, zinc undecylenate, cerium(IV)oxide, uranyl acetate, titanium tetrabutanolate, titanium tetrachloride, titanium tetraphenolate, titanium naphthenate, vanadium(III)chloride, vanadium acetonylacetate, chromium(III)chloride, molybdenum(VI)oxide, molybdenum acetylacetonate, tungsten(VI)oxide, manganese(II)chloride, manganese(II)acetate, manganese(III)acetate, iron(II)acetate, iron(III)acetate, iron phosphate, iron oxylate, iron(III)chloride, iron(III)bromide, cobalt acetate, cobalt chloride, cobalt sulfate, cobalt naphthenate, nickel chloride, nickel acetate, and nickel naphthenate, as well as mixtures of the above.

It has been found to be advantageous to separate the resulting ammonia immediately from the reaction mixture, for example by means of distillation. The apparatus used for this, for example a distillation column, is operated at temperatures from 60° to 150° C., preferably from 65° to 120° C., so that the column does not become coated with ammonium carbamate, which is formed in very small amounts from ammonia and carbon dioxide through the decomposition of urea.

After the reaction is completed, the alcohol, the dialkyl carbonates, and/or other alkyl esters of carbamic acid are separated from the resulting reaction mixture (b) and are held in readiness for reutilization in subsequent batches; with a continuous process, however, they are preferably returned directly to reaction step (a).

As explained above, the separation of the cited compounds is preferably performed in two steps. In the first step the alcohol is distilled off until a residual alcohol content of from 1 to 30 weight percent is obtained, preferably from 2 to 15 weight percent, based on the weight of residual reaction mixture, and said alcohol is returned to reaction step (a).

The undistilled residue of step (i), which for the most part is comprised of 3-alkoxycarbonylaminomethyl-3,5,5-trimethyl-1-alkoxycarbonylaminocyclohexane and, in some cases, isophorone oligourea polyurethanes, as well as the remaining alcohol, dialkyl carbonate, and/or alkyl ester of carbamic acid, is treated in the second step in a stripping column with from 50 to 5000 liters, preferably from 100 to 1000 liters, inert gas per liter of the more concentrated reaction mixture per hour at stripping temperatures from 50° to 200° C., preferably from 120° to 180° C., in order to almost completely separate the remaining alcohol, the dialkyl carbonates, and/or the alkyl esters of carbamic acid. Suitable inert gases which may be used for this process are, for example, nitrogen, carbon monoxide, rare gases, and methane. The stripped, low-boiling point compounds are condensed, in some cases stored for an interim period, and reserved for use in further batches. With the continuous process, they are returned directly to reaction step (a).

The residue obtained after stripping (b), which is primarily comprised of 3-alkoxycarbonylaminomethyl-3,5,5-trimethyl-1-alkoxycarbonylaminocyclohexane and, in some cases, isophorone oligourea polyurethanes, can be evaporated in liquid or solid form or as a melt suspension or in a solvent which is inert under the reaction conditions, said evaporation being performed in a evaporator, and can then be thermally cleaved in a subsequent cleaving reactor.

In the preferred embodiment of the process of the invention, the residue (b) is charged into the evaporator in a solution-free condition in the form of a melt heated to from 80° to 180° C., preferably from 100° to 150° C., by means of a metering pump.

Evaporators which have proven to be particularly effective at temperatures from 200° to 300° C., preferably from 220° to 300° C., and more preferably from 240° to 280° C., and at a pressure from 0.1 to 200 mbar, preferably from 5 to 100 mbar, are film evaporators or fluidized bed evaporators. However, any other evaporators can be used, for example, screw evaporators, A.P. reactors (manufacturer: Krauss-Maffei), metal coil or agitated bed evaporators.

When film evaporators are used, it is indeed possible to evaporate the entire amount of 3-alkoxycarbonylaminomethyl-3,5,5-trimethyl-1-alkoxycarbonylaminocyclohexane charged to the evaporator by using a sufficient amount of heat. However, it is advantageous to discharge part of the charged 3-alkoxycarbonylaminomethyl-3,5,5-trimethyl-1-alkoxycarbonylaminocyclohexane, together with any isophorone oligourea polyurethane that may be present, in an unevaporated form as a melt, since this achieves a significant cleaning effect on the evaporator wall. The weight ratio of evaporated to unevaporated 3-alkoxycarbonylaminomethyl-3,5,5-trimethyl-1-alkoxycarbonylaminocyclohexane can be varied over wide ranges, for example from 20:80 to 90:10. The melt discharged from the evaporator is preferably returned directly to reaction step (a), the diurethanation step.

The 3-alkoxycarbonylaminomethyl-3,5,5-trimethyl-1-alkoxycarbonylaminocyclohexane vapors (c) are charged into the cleaving reactor and are thermally cleaved therein at a temperature in excess of 300°, preferably from 310° to 480° C. and more preferably from 310° to 440° C., and at a reduced pressure, for example, from 0.1 to 200 mbar, preferably from 0.1 to 100 mbar and more preferably from 1 to 50 mbar, in a discontinuous or, preferably, continuous process into IPDI and alcohol.

The cleaving reactor, which generally is of a column-like shape, can have a cross section of any desired shape. Preferably, long, cylinderical cleaving reactors are used. The ratio of the inside diameter to the length of the cleaving reactor is generally from 1:2 to 1:1000, preferably from 1:10 to 1:500. The cleaving reactors can be positioned vertically or horizontally or at positions between vertical and horizontal. Preferably, tubular ovens are used as the cleaving reactors, said tubular ovens having inside tube diameters of approximately 10 to 100 mm and tube lengths of approximately 0.5 to 5 m.

It is desirable to perform the cleavage operation in the presence of thermally stable reactor packing. Suitable packing material includes all temperature-resistant and gas permeable materials such as beads, wool, rings, and/or chips of coal, steel, brass, copper, zinc, aluminum, titanium, chromium, cobalt, nickel and/or quartz. Some of these materials, such as steel, brass, aluminum, and zinc, have proven to be particularly effective and are, therefore, used preferentially, since they produce better cleavage results. Here, it has not yet been determined whether catalytic or physical effects are involved, for example, better heat transfer, or whether a synergistic combination of both effects is involved.

From the cleaving reactor, the dissociation products found in the vapor phase, which consists almost exclusively of IPDI and alcohol, are directed into a two-step vapor condensation device (e). In the first condensation step, which is operated dependent on the system pressure of from 0.1 to 100 mbar at temperatures from 60° to 120° C., the IPDI condenses out almost completely.

When using the preferred 3-butoxycarbonylaminomethyl-3,5,5-trimethyl-1-butoxycarbonylaminocyclohexane, at a system pressure from 20 to 40 mbar it is desirable to maintain a condensation temperature of from 70° to 100° C. In the second condensation step, primarily alcohol is condensed. This alcohol is returned to reaction step (a). The temperature in the second condensation step is based on the boiling point of the alcohol which is to be condensed. In the cleavage of 3-butoxycarbonylaminomethyl-3,5,5-trimethyl-1-butoxycarbonylaminocyclohexane, it is desirable at the above system pressure to maintain a condensation temperature of from 5° to 30° C. The IPDI obtained in the first condensation step is generally subjected to a purification distillation and thereafter is greater than 99.5 weight percent pure. The bottom product resulting from this purification distillation is also returned to reaction step (a).

Depending on the condensation temperatures which are selected and the system pressure which is used, varying amounts of alcohol can be also condensed in the first condensation step and varying amounts of IPDI can also be condensed in the second condensation step. In a preferred embodiment, the IPDI that is also condensed in the second condensation step is allowed to react with excess alcohol to form 3-alkoxycarbonylaminomethyl-3,5,5-trimethyl-1-alkoxycarbonylaminocyclohexane, and after being separated from the alcohol, this is again returned to the evaporation and cleavage steps. However, in another preferred embodiment it is also possible to return the 3-alkoxycarbonylaminomethyl-3,5,5-trimethyl-1-alkoxycarbonylaminocyclohexane together with the dialkyl carbonate and/or alkyl esters of carbamic acid to reaction step (a).

In a similar manner, the alcohol that has also condensed in the first condensation step can be allowed to react with excess IPDI, and the reaction products can be returned to the evaporation and cleaving steps after distillative separation of the IPDI, or, in the preferred embodiment, can be mixed with the alcohol contained in the second condensation step and returned to reaction step (a).

The IPDI prepared in accordance with the process of the invention is extremely suitable for the preparation of polyurethane or polyurethane-polyurea plastics and, in particular, for light-resistant polyurethane paints and coatings.

EXAMPLE

Seventeen hundred parts isophoronediamine, 1200 parts urea, and 370 parts n-butanol were charged into a mixing vessel fitted with a heated column and a pressure regulating valve on top. In addition, 105 parts dibutyl carbonate, 117 parts butyl ester of carbamic acid, 956 parts 3-butoxycarbonylaminomethyl-3,5,5-trimethyl-1-butoxycarbonylaminocyclohexane, and 3288 parts n-butanol, which were obtained from an experiment previously performed in a similar manner were added to this mixture. This reaction mixture was heated for 10 hours at from 210° to 220° C. and under a pressure from 6 to 8 bar. The resulting ammonia was separated from the reaction solution via the column installed on top of the vessel and operated at from 80° to 85° C. with almost complete reflux of the n-butanol. After completion of the reaction, the solution was allowed to depressurize into a packed column operating at standard pressure, from whose head discharge 1923 parts n-butanol were obtained. The bottoms were charged into a stripping column operated at approximately 160° C. Approximately 300 liters of nitrogen per liter reaction mixture per hour was forced through this stripping column as the stripping gas. At the head, a mixture was obtained which contained the butyl ester of carbamic acid, dibutyl carbonate, and n-butanol. The bottoms of the stripping column were charged without cooling and at a pressure of 30 mbar into a film evaporator heated to from 270° to 280° C. in such a manner that the ratio of evaporated 3-butoxycarbonylaminomethyl-3,5,5-trimethyl-1-butoxycarbonylaminocyclohexane to discharging melt was approximately 4:1. The vapors were directed into a cleavage reactor having an empty volumetric capacity of ca. 3 liters. This reactor was packed with brass rings of 3 mm diameter. The temperature in the cleavage reactor averaged 410° C. The exiting cleavage gases were fractionally condensed in a subsequent two-step condensation device. In the first condenser, which was operated at 95° C., a mixture comprising 78 weight percent isophorone diisocyanate, 19 weight percent of a monoisocyanate monourethane (mixed isomers), and 3 weight percent 3-butoxycarbonylaminomethyl-3,5,5-trimethyl-1-butoxycarbonylaminocyclohexane. In a subsequent distillation step, this mixture yielded 1472 parts isophorone diisocyanate of purity >99 percent.

The bottoms of the pure distillation were mixed with the discharge obtained in the second condenser operated at from 10° to 12° C., the discharge from the film evaporator, the head product from the stripping column, and the n-butanol obtained in the first distillation, and this mixture was heated to boiling for two hours. An analysis of this mixture by means of gas chromatography and high pressure liquid chromatography revealed that it contained 113 parts butyl ester of carbamic acid, 102 parts dibutyl carbonate, 3151 parts n-butanol, and 2066 parts 3-butoxycarbonylaminomethyl-3,5,5-trimethyl-1-butoxycarbonylaminocyclohexane, which corresponds to an isophorone diamine to isophorone diisocyanate selectivity of ca. 95 percent.

The embodiments of the invention in which an exclusive privilege or property is claimed are defined as follows:

1. A multiple-step process for the preparation of 3-isocyanatomethyl-3,5,5-trimethyl-cyclohexylisocyanate, wherein
   (a) 3-aminomethyl-3,5,5-trimethylcyclohexylamine is reacted with urea and alcohol in the presence of dialkyl carbonates and/or carbamide acid alkyl esters to form 3-alkoxycarbonylaminomethyl-3,5,5-trimethyl-1-alkoxycarbonylaminocyclohexane while the ammonia produced thereby is simultaneously removed,
   (b) the alcohol, the dialkyl carbonates and/or carbamic acid alkyl esters are removed and, preferably, returned to reaction step (a),
   (c) the 3-alkoxycarbonylaminomethyl-3,5,5-trimethyl-1-alkoxycarbonylaminocyclohexane is evaporated in an evaporator at temperatures from 200° C. to 300° C. and at a pressure of from 0.1 mbar to 200 mbar,
   (d) the vapors are thermally cleaved at temperatures in excess of 300° C. and at a pressure of from 0.1 to 200 mbar in a cleaving reactor into 3-isocyanatomethyl-3,5,5-trimethylcyclohexylisocyanate and alcohol, and
   (e) the cleavage products are fractionally condensed.

2. The process of claim 1 wherein the resulting reaction mixture (b) is separated in two steps, whereby
   (i) in the first step, the alcohol is distilled off until a residual alcohol content of from 1 percent by weight to 30 percent by weight based on the total weight of the residual mixture (b) and the distilled alcohol is returned to reaction step (a) and
   (ii) in the second step, the remaining alcohol, the dialkyl carbonate, and/or the carbamic acid alkyl ester is separated from the 3-alkoxycarbonylaminomethyl-3,5,5-trimethyl-1-alkoxycarbonylamino-cyclohexane by stripping with inert gas and is returned to reaction step (a).

3. The process of claim 2 wherein the stripping is carried out in a stripping column at temperatures from 50° C. to 200° C. with 50 l to 5000 l inert gas per liter of reaction mixture per hour.

4. The process of claim 1 wherein the cleavage products are fractionally condensed in a two-step condensation device, whereby primarily 3-isocyanatomethyl-3,5,5-trimethyl-cyclohexyl isocyanate is condensed in the first step, and mainly alcohol is condensed in the second section of the condensation device, said alcohol being returned to reaction step (a) together with the residues from a subsequent purification distillation of the 3-isocyanatomethyl-3,5,5-trimethyl-cyclohexylisocyanate.

5. The process of claim 1 wherein in reaction step (a) 1.8 to 2.5 moles urea and 2 to 10 moles alcohol are reacted per each mole of 3-aminomethyl-3,5,5-trimethylcyclohexylamine.

6. The process of claim 1 wherein the alcohol used in reaction step (a) is selected from the group consisting of n-propanol, n-butanol and isobutanol.

7. The process of claim 1 wherein in reaction step (a) carbamic acid alkyl ester corresponding to the alcohol is used in amounts from 1 mole percent to 20 mole percent, based on 3-aminomethyl-3,5,5-trimethyl-cyclohexylamine.

8. The process of claim 1 wherein in reaction step (a) the dialkyl carbonate corresponding to the alcohol is used in amounts from 1 mole percent to 30 mole percent based on 3-aminomethyl-3,5,5-trimethyl-cyclohexylamine.

9. The process of claim 1 wherein the ammonia formed in reaction step (a) is removed from the reaction mixture with the aid of a distillation device at temperatures from 60° C. to 150° C.

10. The process of claim 1 wherein a film evaporator is used as the evaporator in step (c) and the 3-alkoxycarbonylaminomethyl-3,5,5-trimethyl-1-alkoxycarbonylamino-cyclohexane are added in such a manner that from 20 percent by weight to 90 percent by weight 3-alkoxycarbonylaminomethyl-3,5,5-trimethyl-1-alkoxycarbonylaminocyclohexane evaporates and 20 percent by weight to 80 percent by weight, together with any isophorone-oligo-urea polyurethanes which may be present, flow off and are returned to reaction step (a).

11. The process of claim 1 wherein the thermal cleavage (d) is performed in the presence of temperature-resistant, gas-permeable packings of steel, brass, copper, zinc, aluminum, titanium, chromium, cobalt, nickel, carbon and/or quartz in the cleaving reactor.

* * * * *

UNITED STATES PATENT AND TRADEMARK OFFICE
CERTIFICATE OF CORRECTION

PATENT NO. : 4,596,679

DATED : June 24, 1986

INVENTOR(S) : Hans Hellbach, Franz Merger and Friedrich Towae

It is certified that error appears in the above-identified patent and that said Letters Patent is hereby corrected as shown below:

Column 7, Claim 1(b), line 64, delete "preferably".

Signed and Sealed this

Sixteenth Day of December, 1986

Attest:

DONALD J. QUIGG

Attesting Officer     Commissioner of Patents and Trademarks